United States Patent
Campbell et al.

(10) Patent No.: US 8,784,734 B2
(45) Date of Patent: Jul. 22, 2014

(54) REUSABLE SHEATHS FOR SEPARATING MAGNETIC PARTICLES

(75) Inventors: Douglas M. Campbell, Highland Village, TX (US); Gregory E. Gardner, Grapevine, TX (US)

(73) Assignee: Abbott Laboratories, Abbott Park, IL (US)

( * ) Notice: Subject to any disclaimer, the term of this patent is extended or adjusted under 35 U.S.C. 154(b) by 521 days.

(21) Appl. No.: 12/783,619

(22) Filed: May 20, 2010

(65) Prior Publication Data

US 2011/0287555 A1 Nov. 24, 2011

(51) Int. Cl.
*G01N 35/00* (2006.01)
*B03C 1/01* (2006.01)
*B03C 1/03* (2006.01)
*G01N 35/10* (2006.01)

(52) U.S. Cl.
CPC .. *G01N 35/0098* (2013.01); *G01N 2035/00574* (2013.01); *G01N 2035/1088* (2013.01); *B03C 1/03* (2013.01); *B01J 2219/00452* (2013.01); *B01J 2219/005* (2013.01); *B01J 2219/00648* (2013.01); *B01J 2219/00655* (2013.01); *B03C 1/01* (2013.01); *B03C 2201/18* (2013.01)
USPC ............................................. 422/64; 422/527

(58) Field of Classification Search
CPC .......... G01N 35/0098; G01N 35/0099; G01N 35/025; G01N 2035/00574; G01N 2035/0439; G01N 2035/0444; G01N 2035/1088; G01N 2035/1086; G01N 2035/1093; B03C 1/01; B03C 1/03; B03C 1/145; B03C 2201/18; B01J 2219/006; B01J 2219/00648; B01J 2219/005; B01J 2219/00452
See application file for complete search history.

(56) References Cited

U.S. PATENT DOCUMENTS

| | | | |
|---|---|---|---|
| 3,121,985 A * | 2/1964 | Harrison | ........................ 53/115 |
| 4,275,149 A | 6/1981 | Litman et al. | |
| 5,183,638 A | 2/1993 | Wakatake | |
| 5,795,784 A | 8/1998 | Arnquist et al. | |
| 5,856,194 A | 1/1999 | Arnquist et al. | |
| 5,942,124 A | 8/1999 | Tuunanen | |
| 6,040,192 A | 3/2000 | Tuunanen | |
| 6,193,892 B1 | 2/2001 | Krueger et al. | |
| 6,207,463 B1 | 3/2001 | Tuunanen | |

(Continued)

FOREIGN PATENT DOCUMENTS

| | | |
|---|---|---|
| EP | 0254051 B1 | 1/1988 |
| EP | 0681700 B1 | 11/1995 |
| EP | 1145010 B1 | 10/2001 |
| WO | 8800695 A1 | 1/1988 |

OTHER PUBLICATIONS

KingFisher™ mL User Manual, Revision 1.0, Feb. 2002, Catalog No. 1508260, pp. 8-13.

(Continued)

*Primary Examiner* — Christopher A Hixson
(74) *Attorney, Agent, or Firm* — Hanley, Flight & Zimmerman, LLC

(57) ABSTRACT

An assembly that utilizes reusable sheaths for covering magnetic rods for collecting particles in an inverse magnetic particle process. The magnetic rod is removed from the reusable sheath to release particles at the same or a different location. The reusable sheaths can be assembled in a cylindrical plate, which can be rotated to position a clean sheath for each step of the inverse magnetic particle process. When not being used for particle separation, the sheaths can be washed of potentially contaminating solution in wash receptacles.

23 Claims, 6 Drawing Sheets

(56) References Cited

U.S. PATENT DOCUMENTS

| | | |
|---|---|---|
| 6,312,910 B1 | 11/2001 | Vellinger et al. |
| 6,325,927 B1 | 12/2001 | Green |
| 6,447,729 B1 | 9/2002 | Tuunanen |
| 6,448,092 B1 | 9/2002 | Tuunanen |
| 6,579,453 B1 | 6/2003 | Bachler et al. |
| 6,596,162 B2 | 7/2003 | Tuunanen |
| 2002/0164807 A1* | 11/2002 | Itaya et al. ............... 436/45 |
| 2009/0181359 A1 | 7/2009 | Lou et al. |
| 2009/0220979 A1* | 9/2009 | Davis et al. .............. 435/6 |
| 2012/0214711 A1* | 8/2012 | Ganz et al. ............... 506/38 |

OTHER PUBLICATIONS

KingFisher™ Micro-well User Manual, Revision 1.0, Apr. 9, 1999, Catalog No. 1507730.

* cited by examiner

REUSABLE SHEATHS FOR SEPARATING MAGNETIC PARTICLES

BACKGROUND OF THE INVENTION

1. Field of the Invention

This invention relates to inverse magnetic particle processing, more particularly, reusable sheaths for magnets.

2. Discussion of the Art

The ThermoFisher Kingfisher™ magnetic particle separation system performs in vitro diagnostic assays. The KingFisher™ mL magnetic particle processor is described in detail in KingFisher™ mL User manual, Revision No. 1.0, February 2002, Catalog No. 1508260, incorporated herein by reference. The KingFisher™ magnetic particle processor is described in detail in KingFisher™ Micro-well User Manual, Revision No. 1.0, 1999-04-09, Catalog No. 1507730, incorporated herein by reference. The KingFisher™ magnetic particle processor is designed for automated transfer and processing of magnetic particles in volumes of liquids suitable for micro-wells. The KingFisher™ mL magnetic particle processor employs greater volumes of liquids than does the KingFisher™ magnetic particle processor. Regardless of which of the aforementioned KingFisher™ instrument is being used, the operating principle employed is inverse magnetic particle processing technology, commonly referred to as MPP. According to inverse magnetic particle processing technology, magnetic particles are transferred with the aid of magnetic rods covered with disposable, specially designed plastic tip combs.

Referring now to FIGS. 1 and 2, a KingFisher™ mL magnetic particle processor 10 can be used for automated transfer and processing of magnetic particles in tubes of a tube strip. In the description that follows, the tubes of the tube embodiment will be used to illustrate the concentrating technique. The principle of the KingFisher™ mL magnetic particle processor 10 is based on the use of (a) magnetic rods 12a, 12b, 12c, 12d, and 12e that can be covered with a disposable tip comb 14 and (b) tube strips 16. A tip comb 14 comprises a strip of non-magnetic material that joins a plurality of sheaths 14a, 14b, 14c, 14d, and 14e made of non-magnetic material for covering magnetic rods. A tube strip 16 is a plurality of tubes 16a, 16b, 16c, 16d, and 16e arranged in a row. The KingFisher™ mL magnetic particle processor 10 is capable of functioning without any aspiration and/or dispensing devices. The KingFisher™ mL magnetic particle processor 10 is designed for a maximum of fifteen (15) tube strips 16, which are compatible with the tip comb 14. The tube strip(s) 16 is (are) maintained stationary and the only movable assembly is a processing head 18 along with the tip combs 14 and magnetic rods 12a, 12b, 12c, 12d, and 12e associated therewith. The processing head 18 comprises two vertically moving platforms 20, 22. One platform 20 is needed for the magnetic rods 12a, 12b, 12c, 12d, and 12e, and the other platform 22 is needed for the tip combs 14. A tray 24 contains 15 separate tube strips 16 and a single sample processing typically uses one tube strip 16 containing five tubes 16a, 16b, 16c, 16d, and 16e. One tip comb 14 containing five sheaths 14a, 14b, 14c, 14d, and 14e is used for processing five samples at one time. In FIG. 2, only one magnetic rod 12a and only one sheath 14a are numbered. Magnetic rods 12b, 12c, 12d, and 12e and sheaths 14b, 14c, 14d, and 14e are not numbered in FIG. 2.

Before starting the magnetic particle processing via a keypad (not shown) and a display (not shown), the samples and reagents are dispensed into the tubes 16a, 16b, 16c, 16d, and 16e and the tip comb(s) 14 is (are) loaded into its (their) slot(s). The tube strip(s) 16 is (are) placed into the removable tray in the correct position and the tray is pushed into the end position. During the operation, the front and top lids can be closed or open. Closed lids protect the processing against environmental contamination.

Rather than moving the liquids from one tube to another tube, the magnetic particles are moved from one tube 16a to another tube 16b, at least one tube containing specific reagent(s). This principle stands in contrast to the external magnet method, i.e., the type of separation used in the apparatus shown in U.S. Pat. Nos. 5,795,784 and 5,856,194.

Working with magnetic particles can be divided into five separate process steps:

Collecting particles: In this step, magnetic particles are collected from the well or tube specified.

Binding particles: In this step, material is collected onto the magnetic particles from the reagent in a specific well or tube.

Mixing particles: In this step, the reagent and particles (if inserted), are mixed with the plastic sheath in a specific well or tube.

Releasing particles: In this step, the collected material is released from the surfaces of the magnetic particles into a specific well or tube.

Washing particles: In this step, the magnetic particles are washed in a specific well or tube.

FIGS. 3A, 3B, 3C, 3D, 3E, and 3F illustrate the sequence of steps employed in collecting, transferring, and releasing magnetic particles from tubes in a KingFisher™ mL magnetic particle processor. During the collection of the magnetic particles, each magnetic rod 12a is substantially completely enclosed in a sheath 14a. See FIG. 3A. Only magnetic rod 12a and only sheath 14a are shown, but four additional magnetic rods 12b, 12c, 12d, and 12e and four additional sheaths 14b, 14c, 14d, and 14e are also employed. The magnetic rod(s) 12a together with the tip comb(s) 14 move slowly up and down in the tube(s) 16a and the magnetic particles "P" are collected onto the wall(s) of the sheath(s) 14a. See FIG. 3B. Only tube 16a is shown, but four additional tubes, aligned with the four additional sheaths 14b, 14c, 14d, and 14e, are also employed. The magnetic rod(s) 12a together with the tip comb(s) 14, having collected the magnetic particles "P", can be lifted out of the tube(s) 16a and transferred into the next tube(s) 16b. See FIG. 3C. After collection of the magnetic particles "P", the magnetic rod(s) 12a together with the tip comb(s) 14 are lifted from the tube(s) 16b, the magnetic rod(s) 12a are lifted off and the tip comb(s) 14 is (are) lowered into the tube(s) 16b containing a reagent. See, for example, FIGS. 3D and 3E. Magnetic particles "P" are released by moving the tip comb(s) 14 up and down several times at considerably high speed until all the particles have been mixed with the substance in tube(s) 16b to carry out the next reaction. See FIG. 3F. Washing the magnetic particles "P" is a frequent and an important phase of the process. Washing is a combination of the release and collection processes in a tube(s) filled with washing solution. To maximize washing efficiency, the magnetic rod(s) 12a together with the tip comb(s) 14 are designed to have minimized liquid-carrying properties. To keep the magnetic particle suspension evenly mixed in long-running reactions, the tip comb(s) 14 can be moved up and down from time to time. The volume of the first tube can be larger than the volume of the next tube for concentration purposes. For additional discussion relating to the KingFisher™ mL magnetic particle processor, see U.S. Patent Application Publication No. US-2009-0181359-A1, published Jul. 16, 2009, incorporated herein by reference.

The ThermoFisher KingFisher™ system utilizes a linear array of magnets along with a linear array of sheaths, i.e., the sheaths of the tip combs. These tip combs are disposed of after each use.

U.S. Pat. No. 5,183,638 discloses an immunity analysis apparatus for use with magnetic particles in which a sample is transferred to a reaction vessel and the reaction vessel is conveyed past several devices for adding and agitating a magnetic particle solution, adding a stroma solution, absorbing the particles to an inner wall of the reaction vessels to remove the reaction solution, adding an enzyme labeling antibody solution, absorbing the particle on an inner wall a second time to remove the resulting solution, adding a stop solution, measuring the result, and cleaning the reaction vessels for reuse. The device additionally has a structure for agitating the magnetic particle reagent solution containers and moving a pipet arm independent of an L-shaped agitating rod arm during a portion of its movement top supply the reaction vessels with the magnetic particle solution.

U.S. Pat. No. 6,193,892 discloses a magnetic particle separation assembly and method for separating a magnetically responsive complex from a non-magnetic test media in which the magnetically responsive complex is suspended. The assembly comprises an invertible rack for holding specimen containers and a magnetic support member for supporting the rack. The magnetic support member has a base and a planar member bisecting the base and extending upwardly therefrom. The planar vertical member has a plurality of magnets embedded therein. The magnets are disposed in a substantially horizontal orientation parallel to the base and spaced from the base. The invertible rack has a slot therethrough dimensioned to accept the planar vertical member of the magnetic support member.

U.S. Pat. No. 6,312,910 discloses a multistage electromagnetic separator is designed to separate magnetically susceptible materials suspended in fluids. The apparatus includes an upper plate and a lower plate set to a fill position and the fluid samples are filled into upper and lower cuvettes. A translating electromagnet energizes to a programmed current level and translates from the bottom of the lower cuvette to the interface of the plates. The translating electromagnet is de-energized, and a holding electromagnet is energized to a programmed current level pulling particles within a specified mobility range into the top of the captured upper collection cuvette. The holding electromagnet is de-energized leaving the permanent holding magnet to keep the collected sample particles in the top cuvette while the upper plate rotates thereby capturing the sample of the collected particles. The process can be preprogrammed to vary or remain the same for a plurality of captured cuvettes.

U.S. Pat. No. 6,325,927 discloses a magnetic separator apparatus having a configuration of barium ceramic magnets impregnated into polypropylene bars interspersed onto a conveyor belt which passes through an aqueous solution containing unwanted magnetic particulate. A plurality of spaced-apart magnet pairs embedded in each polypropylene bar are configured to provide maximum field penetration and holding strength of the magnets. Particulate attracted to the plurality of magnet pairs are scraped from the conveyor belt into a collection drawer.

U.S. Pat. No. 6,579,453 discloses an apparatus for separating magnetic particles in suspension in a liquid contained in a reaction vessel of the type used in an automatic apparatus for processing biological samples. The apparatus comprises a rotatable carrier holding an array of magnet elements positioned on the carrier at different distances from the rotation axis of the carrier and at different azimuth angles. The carrier and the array of magnet elements can be positioned at a plurality of predetermined angular positions and heights.

None of the foregoing references disclose an inverse magnetic particle processing apparatus capable of reusing sheaths 14a, 14b, 14c, 14d, and 14e. Accordingly, it is desired to develop an apparatus and method for transferring reacting particles from one reaction vessel to another while preventing contamination and at the same time reducing, or even eliminating, the quantity of solid biohazardous material that is generated during the operation of the apparatus and method.

SUMMARY OF THE INVENTION

In one aspect, the invention described herein provides an assembly that employs reusable sheaths for inverse magnetic particle processing. Plastic molded sheaths, arranged in an array in a sheath retainer, are used with permanent magnets in order to prevent particles from sticking to the magnets, but allow for collection of magnetic particles from a liquid solution. The sheaths are used to mix both the heterogeneous solution and to provide protection of the magnet. The collected particles can be washed by other solutions while being retained on the sheath-encased magnet. Upon completion of washing, the magnet will be retracted from the sheath, thereby allowing the particles to be redispersed into the reaction vessel.

The sheath retainer can be indexed one or more positions so that a clean sheath is available for the next inverse magnetic particle process. The sheath retainer preferably contains teeth completely surrounding the periphery of the sheath retainer, in order to drive the sheath retainer to each of the reaction vessels or wash receptacles. The number of teeth is dependent upon the number of sheaths, spacing of sheaths, and rotational angle necessary to bring the sheath to the proper orientation for either transfer of particles from one tube to another or for washing the sheath in a wash receptacle. The sheath retainer can be driven by a stepper motor having a gear integrated into the plate. Other means of indexing include, for example, a Geneva mechanism, a belt drive system, and a chain and sprocket drive system.

The sheaths not involved in the collection process for the particles can be subjected to a washing regimen so that the sheaths can be reused a plurality of times prior to being replaced. This washing process allows for elimination of, or at least the reduction of, solid waste from the system. The reaction vessels can be formed of glass or of molded plastic and can be reused as well.

In another aspect, the invention provides a system for transferring particles from one tube to another in an inverse magnetic particle processor, which system is further capable of washing sheaths used in the particle transfer process so that they can be reused several times prior to being discarded as solid waste.

DETAILED DESCRIPTION

Figure 1:
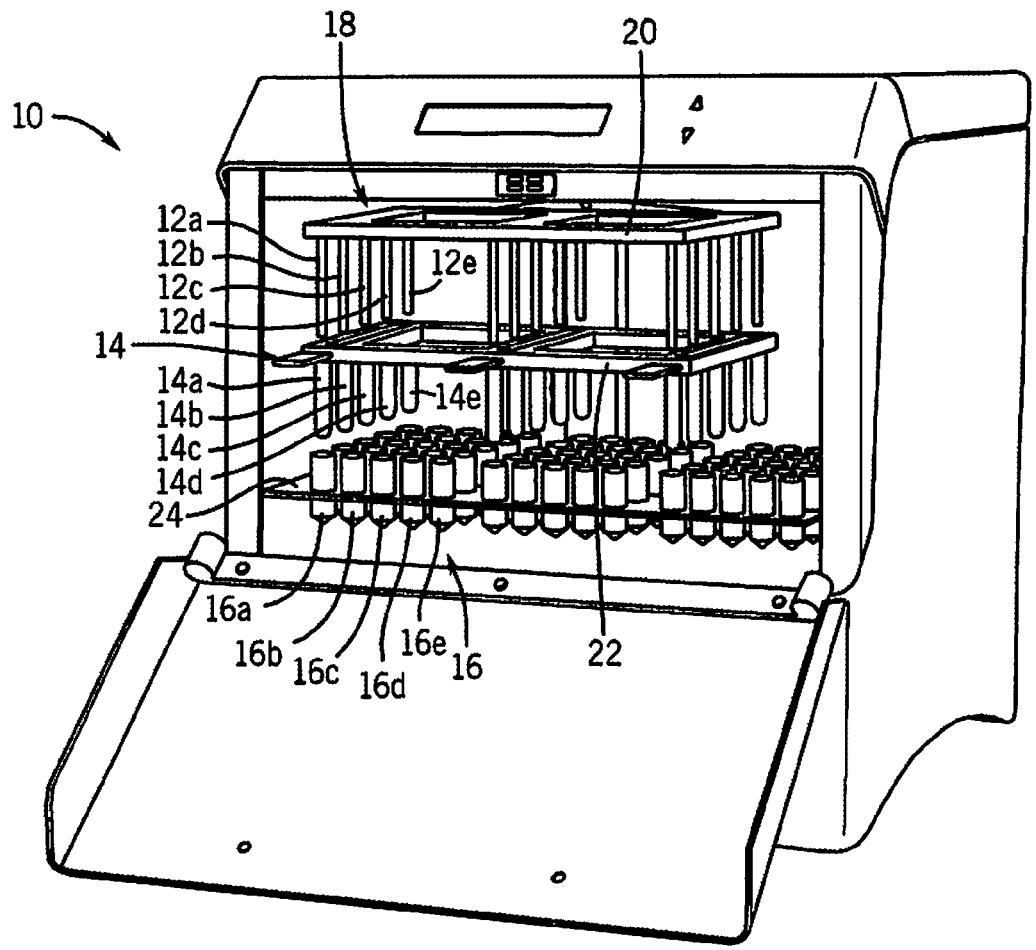
FIG. 1 is a perspective view of a KingFisher™ mL magnetic particle processor.

As used herein, the term "magnetic microparticles" means paramagnetic microparticles. Paramagnetic microparticles are attracted to magnetic fields, hence have a relative magnetic permeability greater than one. However, unlike ferromagnets, which are also attracted to magnetic fields, paramagnetic materials do not retain any magnetization in the absence of an externally applied magnetic field.

As used herein, the expressions "label", "label group", and the like mean a group attached to a specific binding member, e.g., an antibody or an antigen, to render the reaction between the specific binding member and its complementary binding member detectable. Representative examples of labels include enzymes, radioactive labels, fluorescein, and chemicals that produce light. A label is any substance that can be attached to an immunoreactant and that is capable of producing a signal that is detectable by visual or instrumental means. Various labels suitable for use in this invention include catalysts, enzymes, liposomes, and other vesicles containing signal producing substances such as chromogens, catalysts, fluorescent compounds, chemiluminescent compounds, enzymes, and the like. A number of enzymes suitable for use as labels are disclosed in U.S. Pat. No. 4,275,149, incorporated herein by reference. Such enzymes include glucosidases, galactosidases, phosphatases and peroxidases, such as alkaline phosphatase and horseradish peroxidase, which are used in conjunction with enzyme substrates, such as fluorescein di(galactopyranoside), nitro blue tetrazolium, 3,5',5,5'-tetranitrobenzidine, 4-methoxy-1-naphthol, 4-chloro-1-naphthol, 4-methylumbelliferyl phosphate, 5-bromo-4-chloro-3-indolyl phosphate, chemiluminescent enzyme substrates, such as the dioxetanes described in WO 88100694 and EP 0-254-051-A2, and derivatives and analogues thereof. Preferably, the label is an enzyme and most preferably the enzyme is alkaline phosphatase.

As used herein, the expression "test sample", the expression "biological sample", and the term "sample" refer to a material suspected of containing an analyte. The test sample can be used directly as obtained from the source or following a pretreatment to modify the character of the sample. The test sample can be derived from any biological source, such as a physiological fluid, such as, for example, blood, saliva, ocular lens fluid, cerebral spinal fluid, sweat, urine, milk, ascites fluid, synovial fluid, peritoneal fluid, amniotic fluid, and the like. The test sample can be pretreated prior to use, such as preparing plasma from blood, diluting viscous fluids, and the like. Methods of treatment can involve filtration, distillation, extraction, concentration, inactivation of interfering components, the addition of reagents, and the like. Other liquid samples besides physiological fluids can be used, such as water, food products, and the like, for the performance of environmental or food production assays. In addition, a solid material suspected of containing the analyte can be used as the test simple. In some instances it may be beneficial to modify a solid test sample to form a liquid medium or to release the analyte.

As used herein, the expressions "solid phase", "solid phase material", and the like, mean any material that is insoluble, or can be made insoluble by a subsequent reaction. Representative examples of solid phase material include polymeric or glass beads, microparticles, tubes, sheets, plates, slides, wells, tapes, test tubes, or the like.

As used herein, the term "analyte" means the compound to be detected or measured. The analyte has at least one epitope or binding site.

As used herein, the symbol "(s)" following the name of an item indicates that one or more of the subject items is intended, depending upon the context.

As used herein, the term "immunoassay" means a special class of assay or test that is performed in a container, e.g., a test tube, which assay or test uses an antibody-antigen reaction to determine whether a patient has been exposed to the antigen or has an antibody to the antigen. An immunoassay can be a heterogeneous immunoassay or a homogeneous immunoassay. The method described herein is primarily concerned with the heterogeneous immunoassay.

Heterogeneous immunoassays can be performed in a competitive immunoassay format or in a sandwich immunoassay format. In the competitive immunoassay format, an antigen can be immobilized to a solid phase material. The amount of detectable moiety that binds to the solid phase material can be detected, measured, and correlated to the amount of antibody (antigen) present in the test sample. Examples of solid phase materials include beads, particles, microparticles, and the like.

The present invention is concerned primarily with the sandwich immunoassay format. However, other immunoassay formats can be used in place of a sandwich immunoassay format. In the sandwich assay immunoassay format, a solid phase, e.g., a microparticle, is coated with antibodies. The antibody on the solid phase is known as the capture antibody. The assay is intended to detect and measure antigens in the sample. A second antibody is labeled with an appropriate label, e.g., acridinium. The second antibody is not attached to a solid phase. The second antibody is known as the detection antibody. The antibody and antigen attach in the following order: antibody on solid phase-antigen-antibody having a label. The solid phase is removed. The antibody-antigen-antibody sandwich enables measurement of the antigen by activating the label, which can be used to determine the concentration of analyte in the sample. As used herein, the expression "sandwich complex" means an antibody-antigen-antibody sandwich.

In one example of the sandwich immunoassay format, a test sample containing an antibody is contacted with an antigen, e.g., a protein that has been immobilized on a solid phase material thereby forming an antigen-antibody complex. Examples of solid phase materials include beads, particles, microparticles, and the like. The solid phase material containing the antigen-antibody complex is typically treated for example with a second antibody that has been labeled with a detectable moiety. The second antibody then becomes bound to the antibody of the sample that is bound to the antigen immobilized on the solid phase material. Then, after one or more washing steps to remove any unbound material, an indicator material, such as a chromogenic substance, is introduced to react with the detectable moiety to produce a detectable signal, e.g. a color change. The color change is then detected, measured, and correlated to the amount of antibody present in the test sample. It should also be noted that various diluents and buffers are also required to optimize the operation of the microparticles, antigens, conjugates and other components of the assay that participate in chemical reactions. It should be further noted that other types of sandwich assays can be utilized, such as, for example, where the first antibody is immobilized on the solid phase material.

A heterogeneous immunoassay to determine the concentration of an analyte present at a low concentration in a biological sample can be performed with the apparatus described in U.S. Pat. Nos. 5,795,784 and 5,856,194, in a sandwich immunoassay format, which employs microparticles as the solid phase material. These patents are incorporated herein by reference.

Figure 4:
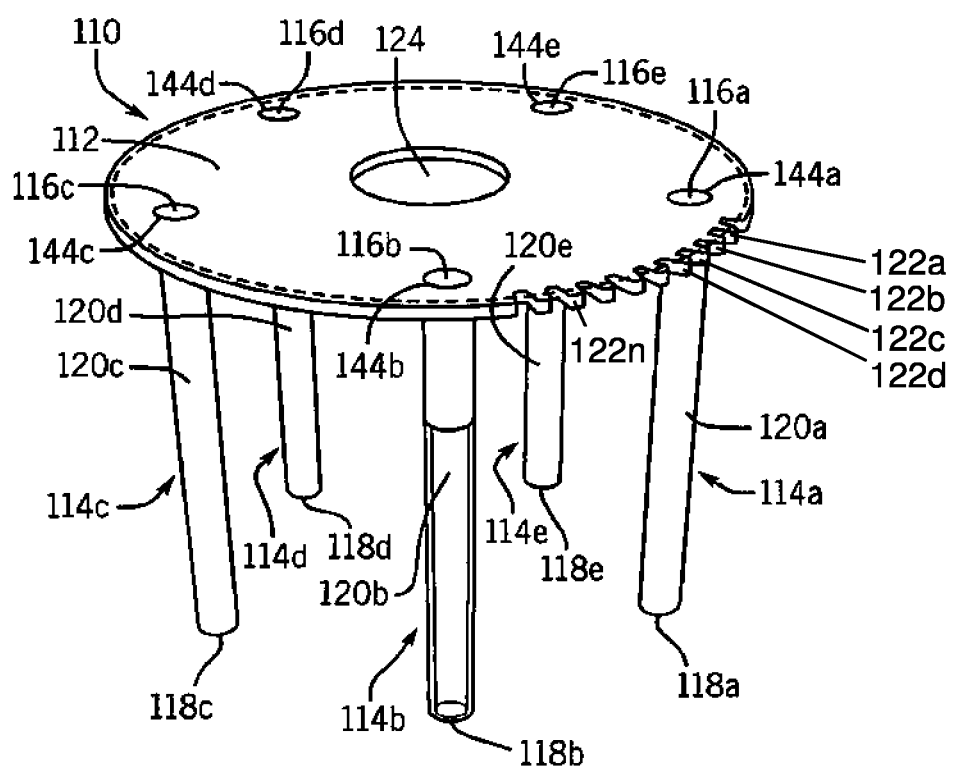
FIG. 4 is a perspective view of an assembly that employs reusable sheaths for inverse magnetic particle processing.

Referring now to FIG. 4, an assembly 110 for washing, positioning, and activating tubular sheaths for processing magnetic microparticles comprises a sheath retainer 112 from which a plurality of elongated sheaths 114a, 114b, 114c, 114d, 114e depend. The sheath retainer 112 is in the shape of a cylindrical plate. For the sake of simplification, the sheath retainer 112 will be alternatively referred to herein as a cylindrical plate 112. Each elongated sheath 114a, 114b, 114c, 114d, 114e has an open end 116a, 116b, 116c, 116d, 116e, respectively, and a closed end 118a, 118b, 118c, 118d, 118e, respectively. Magnetic rods (not shown) can be inserted into the open ends 116a, 116b, 116c, 116d, and 116e of the elongated sheaths 114a, 114b, 114c, 114d, and 114e, respectively. Between the open end 116a, 116b, 116c, 116d, 116e and the closed end 118a, 118b, 118c, 118d, 118e of the elongated sheaths 114a, 114b, 114c, 114d, 114e, respectively, is a tubular portion 120a, 120b, 120c, 120d, and 120e. The tubular portions 120a, 120b, 120c, 120d, and 120e are of sufficient dimensions to enclose and retain magnetic rods. Elongated sheath 114c shows a portion of the wall of the tubular portion cut away to indicate that the tubular portion comprises a wall surrounding a bore. At least a portion of the periphery of the cylindrical plate 112 is characterized by a plurality of teeth 122a, 122b, 122c, 122d, 122n. The cylindrical plate 112 has an aperture 124 formed in center thereof. The aperture 124 passes through both major surfaces of the cylindrical plate 112.

Figure 2:
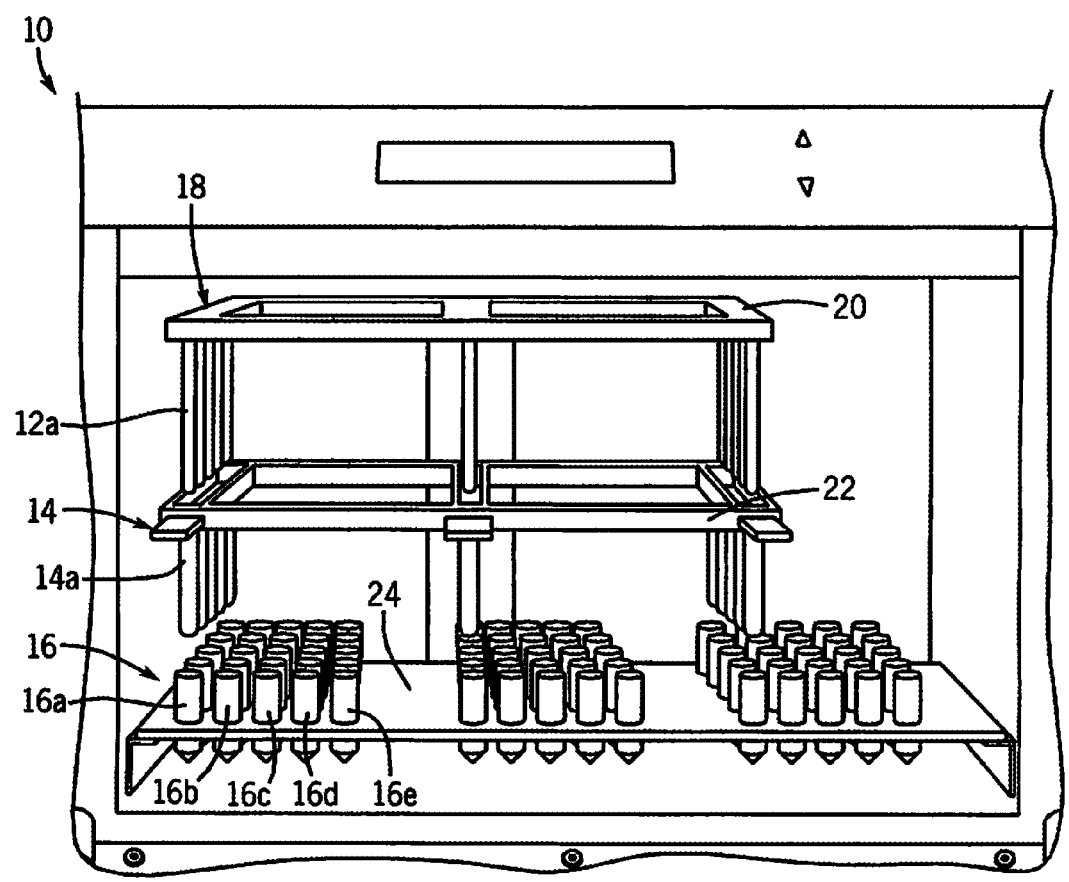
FIG. 2 is a front view in elevation illustrating a KingFisher™ mL magnetic particle processor suitable for carrying out the procedure of inverse magnetic particle processing to prepare a sample for an immunoassay.
Figure 3:
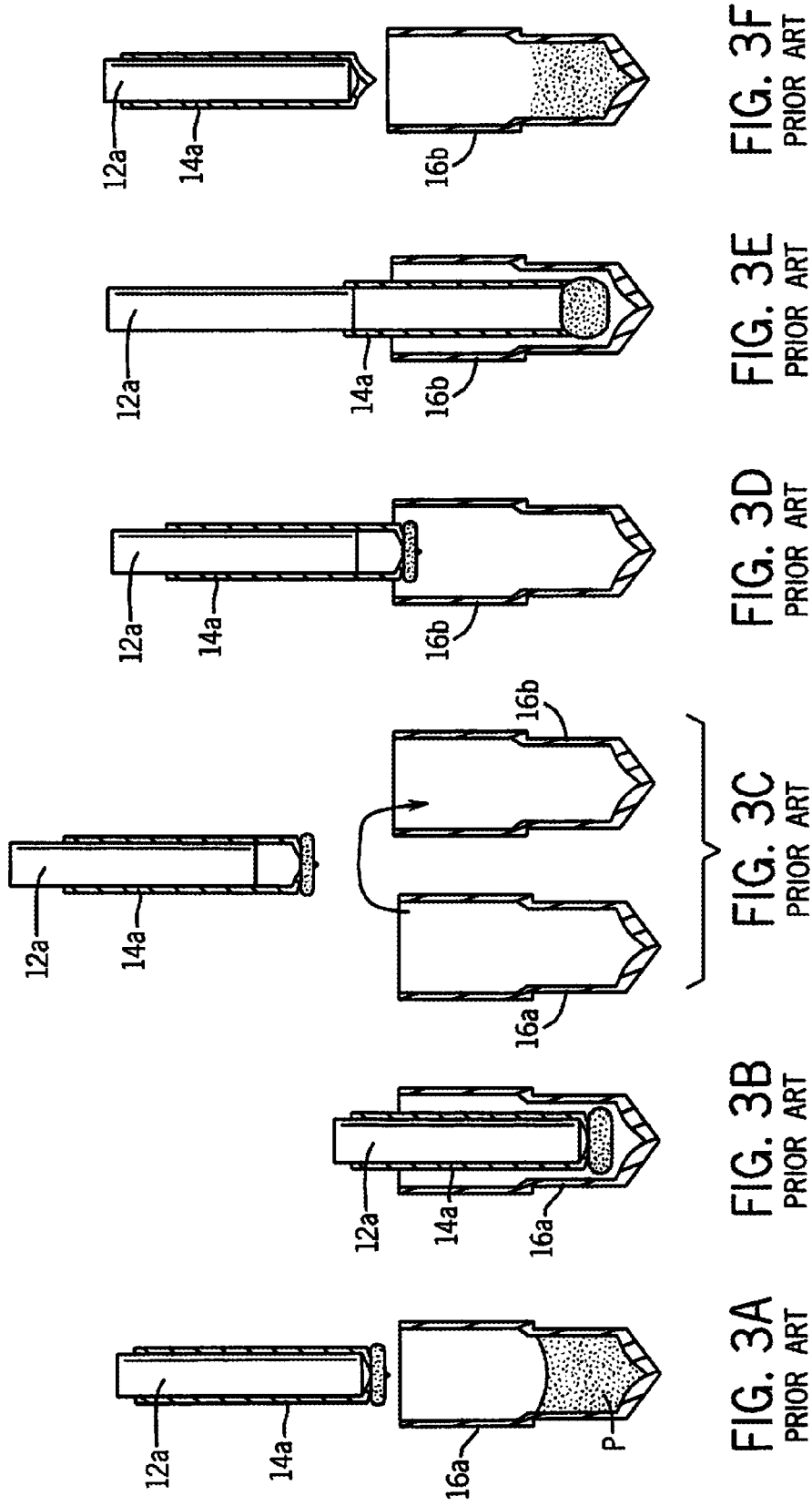
FIGS. 3A, 3B, 3C, 3D, 3E, and 3F constituting a series of schematic diagrams illustrating the procedure of inverse magnetic particle processing utilized by a KingFisher™ mL magnetic particle processor.
Figure 5:
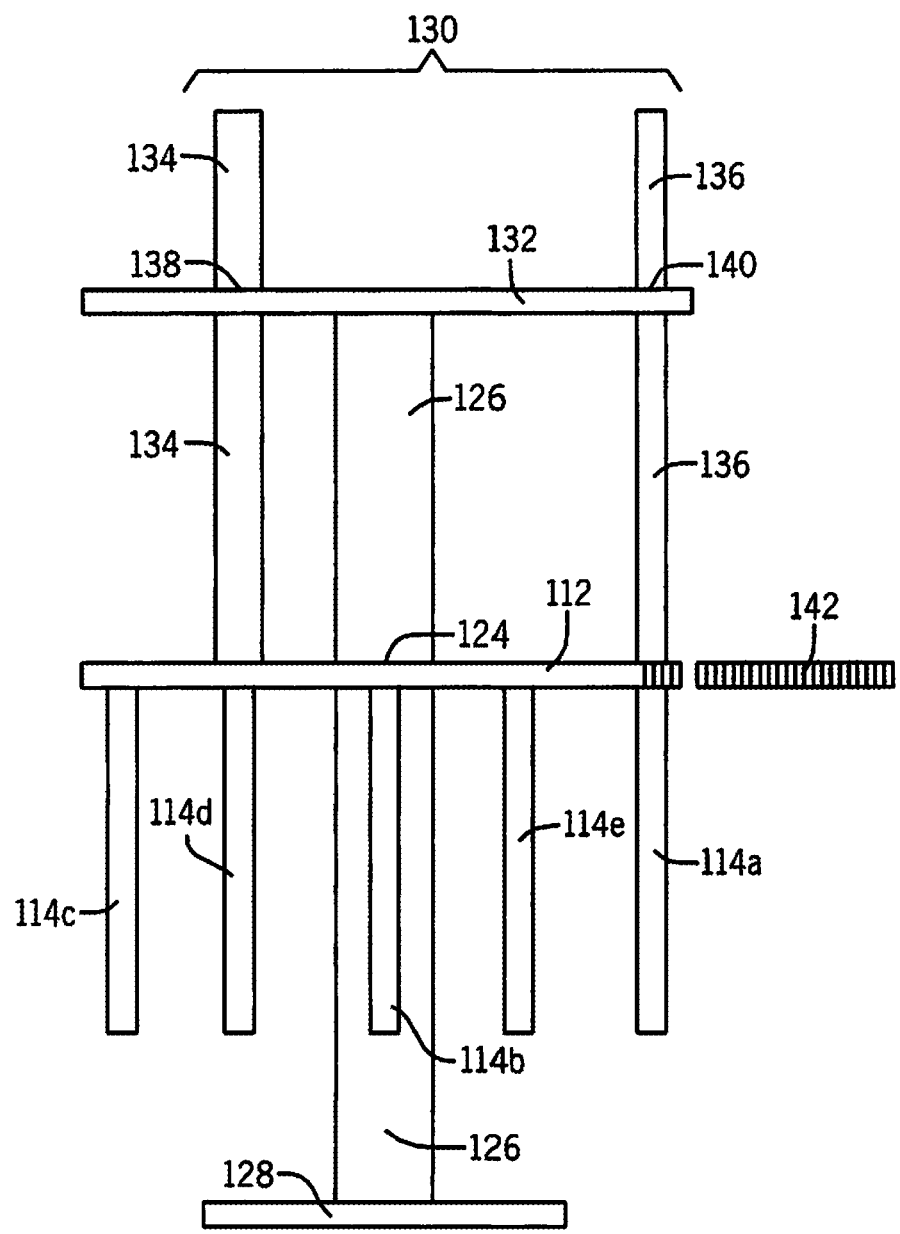
FIG. 5 is a schematic side view in elevation of an assembly that employs reusable sheaths for inverse magnetic particle processing, wherein the assembly is a cylindrical plate mounted on a post extending through an aperture in the center of the cylindrical plate. Also shown in FIG. 5 is a processing head for raising and lowering the cylindrical plate and a drive gear capable of rotating the cylindrical plate.

Referring now to FIG. 5, the purpose of the aperture 124 is to receive and accommodate a post 126, which post 126 provides an axis about which the cylindrical plate 112 can be rotated. The post 126 is affixed to a base 128. The aperture is preferably equipped with a bearing (not shown) to facilitate the rotation of the cylindrical plate 112 about the post 126. A processing head 130 attached to the cylindrical plate 112 enables the cylindrical plate 112 to be raised and lowered so that the elongated sheaths 114a, 114b, 114c, 114d, and 114e can be inserted into and lifted out of reaction vessels as required and inserted into and lifted out of wash receptacles as required. The processing head 130 operates under the same principles as does the processing head shown in FIGS. 1 and 2. In one embodiment, the processing head 130 comprises a guide plate 132 affixed to the post 126, a first lifter 134 attached to a major surface of the cylindrical plate 112 for raising and lowering the cylindrical plate 112, and a second lifter 136 attached to the proximal end of a magnetic rod for lifting the magnetic rod from an elongated sheath and lowering the magnetic rod into an elongated sheath. The first lifter 134 is an elongated element that passes through an aperture 138 in the guide plate 132, and the second lifter 136 is an elongated element that passes through an aperture 140 in the guide plate 132. In other embodiments the first lifter 134 and the second lifter 136 need not be integrated with the post 126. The first lifter 134 can be caused to move either upwardly or downwardly by means of a stepper motor (not shown) in communication with the first lifter 134, and the second lifter 136, can be caused to move upwardly or downwardly by means of a stepper motor (not shown) in communication with the second lifter 136. In general, the processing head 130 performs the dual functions of (a) raising and lowering the cylindrical plate 112 and (b) lifting the magnetic rod out of an elongated sheath and reinserting the magnetic rod into the elongated sheath. The cylindrical plate 112 can be rotated about the post 126 positioned in the aperture 124 by means of a gear drive mechanism, wherein the teeth (not shown) of a drive gear 142 mesh with the teeth 122a, 122b, 122c, 122d, . . . 122n on the periphery of the cylindrical plate 112. Rotation of the cylindrical plate 112 is required when a clean elongated sheath is needed for an inverse magnetic particle process. One of ordinary skill in the art can position the post 126, the processing head 130, the gear drive mechanism, and the drive gear 142 so that the assembly 110 can carry out the functions for which it is intended.

An alternative embodiment of a processing head suitable for use herein can comprise a linear solenoid valve, which can move the assembly 110 in a vertical direction upwardly and downwardly. Another alternative embodiment of a processing head can comprise a linear slide bearing mechanism driven by a motor.

The cylindrical plate 112 also has a plurality of apertures 144a, 144b, 144c, 144d, and 144e radially spaced from the center of the cylindrical plate 112. The apertures 144a, 144b, 144c, 144d, and 144e pass through both major surfaces of the cylindrical plate 112. Each of the radially spaced apertures 144a, 144b, 144c, 144d, and 144e receives an elongated sheath 114a, 114b, 114c, 114d, and 114e, respectively. The sheaths 114a, 114b, 114c, 114d, and 114e can be retained in the apertures 144a, 144b, 144c, 144d, and 144e by means of a friction fit, by means of collars (not shown) formed at the open end of the elongated sheath, by means of rings formed near the open end 116a, 116b, 116c, 116d, 116e, which rings are capable of being snap fit into a slot in the wall of the aperture 144a, 144b, 144c, 144d, and 144e, by means of rings formed in the wall of the aperture 144a, 144b, 144c, 144d, and 144e, which rings are capable of being snap fit into a slot near the open end 116a, 116b, 116c, 116d, 116e of the elongated sheath 114a, 114b, 114c, 114d, 114e, respectively, or by some other fitting technique.

The cylindrical plate 112 is preferably formed of a durable, water-resistant, corrosion-resistant material, such as, for example, a metal, an alloy, or a polymeric material. The areal dimensions of the cylindrical plate 112 should be sufficient to accommodate a plurality of elongated sheaths. The thickness of the cylindrical plate 112 should be sufficient to provide the desired level of rigidity to the cylindrical plate 112. The elongated sheaths 114a, 114b, 114c, 114d, 114e are preferably formed from a polymeric material. The material for forming the elongated sheaths 114a, 114b, 114c, 114d, and 114e should not be magnetic. The length and cross-sectional dimension(s), e.g., diameter, of the elongated sheath 114a, 114b, 114c, 114d, and 114e should be sufficient to accommodate a magnetic rod. Additional information relating to the design of magnetic rods and elongated sheaths can be found in U.S. Pat. Nos. 5,942,124; 6,040,192; 6,207,463 B1; 6,447, 729 B1; 6,448,092 B1; 6,596,162 B2 and European Patent Specification 0 681 700 B1, all of which are incorporated herein by reference.

Figure 6:
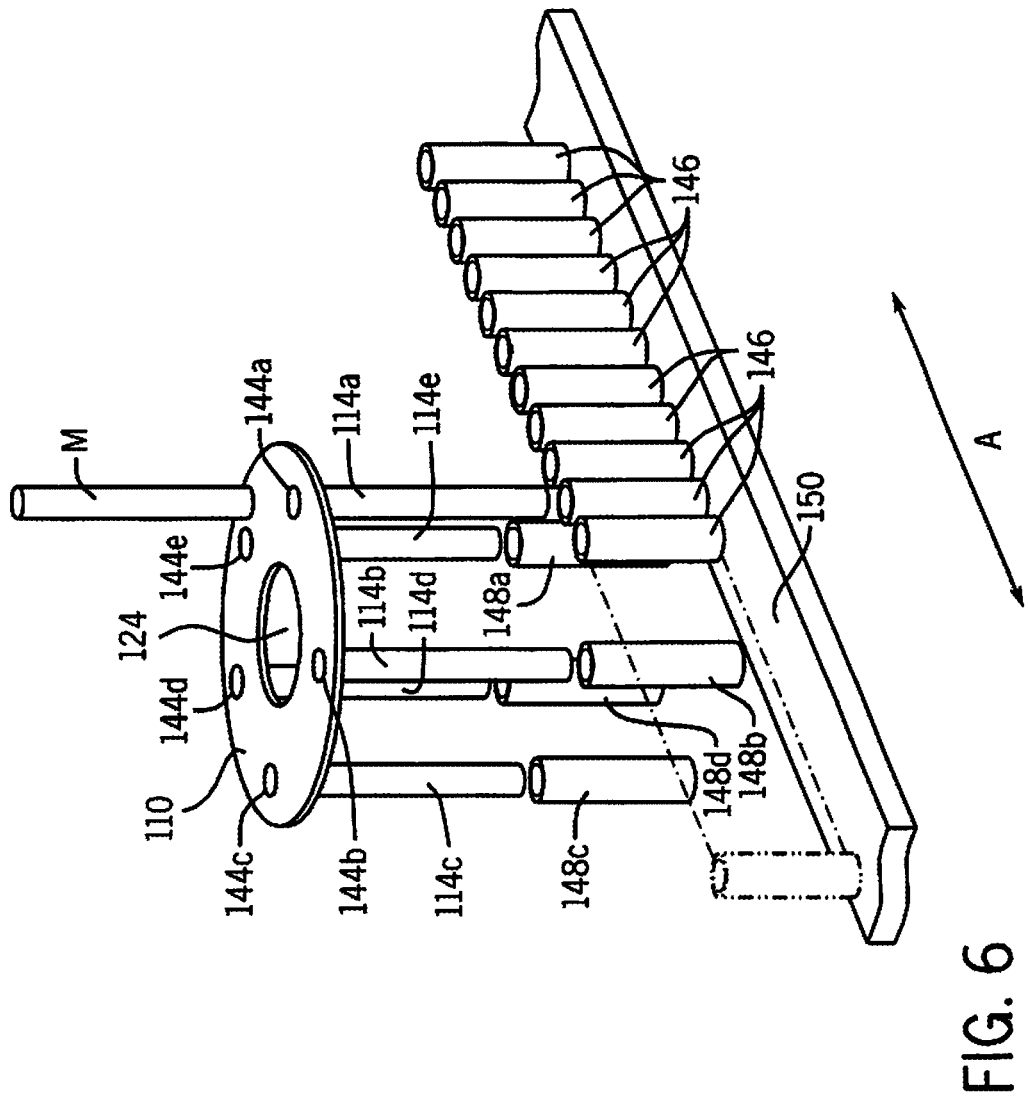
FIG. 6 is a perspective view of the assembly of FIG. 4 illustrating one sheath of the assembly entering a reaction vessel while the remaining sheaths of the assembly are being washed.

Referring now to FIG. 6, a plurality of reaction vessels 146 are arranged in a row. In FIG. 6, for the sake of simplification, each of the reaction vessels 146 has the same reference numeral. The reaction vessels 146 are depicted as tubular in shape. The reaction vessels 146 are preferably made of a non-magnetic material, such as for example, a polymeric material or glass. A plurality of wash receptacles 148a, 148b, 148c, and 148d are arranged in such a manner that the elongated sheaths 114a, 114b, 114c, 114d, 114e can be inserted into the wash receptacles 148a, 148b, 148c, and 148d when it is desired to wash particulate residue from the exterior surfaces of the elongated sheaths 114a, 114b, 114c, 114d, and 114e.

The shapes and the dimensions of the elongated sheaths, the wash receptacles, and the reaction vessels are selected so that the elongated sheaths are compatible with the wash receptacles and the reaction vessels, i.e., the elongated sheaths (a) can retain magnetic rods, (b) can carry out inverse magnetic particle processing by means of the reaction vessels, and (c) can have the entire exterior surfaces of the elongated sheaths washed in the wash receptacles.

As previously indicated, the assembly 110 for washing, positioning, and activating tubular sheaths for processing magnetic microparticles can be mounted on the post 126, the cylindrical plate 112 can be moved upwardly and downwardly as required by the processing head 130, and the cylindrical plate 112 can be rotated by a gear drive mechanism having a drive gear 142. The drive gear 142 itself can be caused to rotate by means of a motor, typically a stepper motor. By means of the aforementioned post 126, processing head 130, and gear drive mechanism, the assembly 110 can be moved to mix reaction mixtures or to collect magnetic particles in a solution or to both mix reaction mixtures and to collect magnetic particles in a solution. In addition, the assembly 110 can carry out the functions of releasing magnetic particles as required and washing magnetic particles as required. A sub-system controlled by a computer can be used to drive the mechanisms that move the cylindrical plate 112. The cylindrical plate 112 can be rotated by the drive gear 142 of the drive gear mechanism so that an elongated sheath, either enclosing a magnetic rod or not enclosing a magnetic rod, can be inserted into a plurality of reaction vessels so that a desired step(s) of an inverse magnetic particle process can be carried out. Alternatives to a drive gear mechanism suitable for rotating the cylindrical plate 112 include, but are not limited to, a Geneva system, a belt drive system, and a chain and sprocket drive system.

Polymeric materials suitable for preparing the components of the assembly 110 for washing, rotating, and activating a tubular sheath for processing magnetic microparticles, other than the magnetic rods, include water-resistant and corrosion resistant polymeric materials, such as, for example, polypropylene, polyurethane, polycarbonate, various polyesters, polystyrene. The process for molding the assembly 110 for washing, rotating, and activating a tubular sheath for processing magnetic microparticles is a limiting factor in constructing the apparatus, along with the tolerances around the wall of the tube.

It should be noted that the components peripheral to the assembly 110, i.e., the post 126, the base 128, the components of the processing head 130, and the drive gear mechanism can be made of polymeric materials, such as, for example, polypropylene, polyurethane, polycarbonate, various polyesters, polystyrene. It should also be noted that these peripheral components can also be made of other materials, such as, for example, corrosion-resistant materials, typically corrosion resistant metals.

In another embodiment, the cylindrical plate 112 can be replaced by a pair of single units (not shown), each of which would comprise an elongated sheath. The single units would be mounted in a carrier suitable for moving the sheaths between reaction vessels and wash receptacles, so that the single units would be alternated between the inverse magnetic particle process and the washing process for the elongated sheath.

The reusable feature of the assembly described herein enables the assembly to be used for numerous diagnostic tests, thereby reducing the level of solid waste generated by inverse magnetic particle processing.

Operation

In order to utilize the apparatus described herein, a number of elongated sheaths (N) are selected and a number of wash positions (N−1) are selected. The value of N preferably ranges from about five (5) to about eight (8). The reactions vessels preferably have a maximum volume approximately equivalent to the volume of a reaction vessel used with the apparatus described in U.S. Pat. Nos. 5,795,784 and 5,856,194, both of which are incorporated herein by reference. The reaction vessels have a shape that is compatible with the elongated sheaths.

As shown in FIG. 6, all of the elongated sheaths 114b, 114c, 114d, and 114e, except for the elongated sheath 114a currently being employed in a magnetic particle processing operation, are undergoing a washing process. The elongated sheath 114a being used for inverse magnetic particle processing can be inserted into various reaction vessels 146. In FIG. 6, the reaction vessels 146 are placed in a linear arrangement. In order for the magnetic rod "M" enclosed in an elongated sheath 114a or the elongated sheath 114a itself (i.e., an elongated sheath not containing a magnetic rod) to be inserted into more than one of the reaction vessels 146 shown, the reaction vessels 146 can be mounted on a movable platform 150 that can be moved as required in order to align the elongated sheath 114a with the appropriate reaction vessel 146, i.e., the reaction vessel 146 appropriate for the process step required to be carried out at a given moment. In this embodiment, the post 126 and the base 128 would remain stationary. In an alternative embodiment, the cylindrical plate 112 can be moved as required in order to align the elongated sheath 114e with the appropriate reaction vessel 146, i.e., the reaction vessel 146 appropriate for the process step required to be carried out at a given moment. In this alternative embodiment, the reaction vessels 146 would remain stationary. However, care must be taken so that the elongated sheaths do not collide with the wash receptacles 148a, 148b, 148c, 148d as the post 126 and the base 128 are being moved. The arrow "A" indicates the direction of movement of the reaction vessels 146 or, in the alternative embodiment, the direction of movement of the post 126 and the base 128. Thus, it is readily apparent that the elongated sheath 114a can be inserted into any of the reaction vessels 146 shown in FIG. 6 in order to carry out various steps of an inverse magnetic particle processing operation. One of ordinary skill in the art can design a magnetic particle processing operation whereby an appropriate immunoassay or other process requiring collecting steps, mixing steps, transfer steps, and washing steps can be carried out. It should also be noted that additional cylindrical plates 112 can be employed to increase the throughput of the inverse magnetic particle processing operation. As the inverse magnetic particle processing operation is being carried out with one elongated sheath 114a, the other elongated sheaths 114b, 114c, 114d, and 114e in the cylindrical plate 112 are being washed in wash receptacles 148b, 148c, 148d, and 148a, respectively. Wash fluid can be supplied to the wash receptacles 148a, 148b, 148c, 148d by a system of wash fluid reservoirs (not shown), pumps (not shown), conduits (not shown). Spent wash fluid can be removed from the wash receptacles 148*a*, 148*b*, 148*c*, and 148*d* by a liquid waste system (not shown).

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus comprising:
   a post having a longitudinal axis;
   a retainer comprising a plate having a plurality of sheath apertures radially spaced from a center of the retainer and a post aperture to receive the post, wherein the retainer is rotatably coupled to the post and movable along the longitudinal axis of the post; and
   a plurality of sheaths removably disposed within the sheath apertures to depend from the retainer.

2. The apparatus of claim 1, wherein the plate comprises teeth on a peripheral edge of the plate.

3. The apparatus of claim 2 further comprising a drive to engage the teeth to rotate the retainer relative to the post.

4. The apparatus of claim 3, wherein the drive comprises one of a Geneva mechanism, a belt drive or a sprocket drive.

5. The apparatus of claim 1 further comprising a processing head to move the retainer in a substantially vertical direction along the post.

6. The apparatus of claim 5, wherein the processing head includes a first lifter coupled to a major surface of the plate.

7. The apparatus of claim 5 further comprising a magnetic rod, wherein the processing head is to move the magnetic rod into any one of the sheaths.

8. An apparatus comprising:
   a post having a longitudinal axis;
   a plate having a first major surface, a second major surface opposite the first major surface, and a third surface between the first major surface and the second major surface, the third surface having a plurality of teeth, the plate having a plurality of sheath apertures and a post aperture extending through the first and second major surfaces thereof, the post aperture to receive the post, wherein the plate is rotatable about the longitudinal axis of the post and movable along the longitudinal axis of the post; and
   a plurality of sheaths having an open top end and a closed bottom end, the sheaths to be removably disposed within the sheath apertures to depend downwardly from the plate.

9. The apparatus of claim 8, wherein the plate is substantially cylindrical shaped.

10. The apparatus of claim 8, wherein the sheath apertures are spaced radially on the plate.

11. The apparatus of claim 8 further comprising a gear drive to engage the teeth to rotate the plate.

12. The apparatus of claim 11, wherein the gear drive comprises a stepper motor.

13. The apparatus of claim 8, wherein the sheaths are retained within the sheath apertures via a friction fit.

14. The apparatus of claim 8, wherein the sheaths comprise collars formed at the open top ends of the sheaths, the collars to retain the sheaths within the sheath apertures.

15. The apparatus of claim 8 further comprising:
   rings formed near the open top ends of the sheaths that fit within slots in the sheath apertures, the rings to retain the sheaths within the sheath apertures; or
   rings formed within walls of the sheath apertures that fit into slots near the open top ends of the sheaths, the rings to retain the sheaths within the sheath apertures.

16. An apparatus comprising:
   a post having a longitudinal axis;
   a sheath retainer to hold a plurality of sheaths, the sheath retainer comprising a plate having a plurality of sheath apertures spaced radially on the plate and an aperture to receive the post;
   a plurality of sheaths to receive a magnetic rod, each of the sheaths having an open end and closed end, the sheaths removably disposed within the sheath apertures;
   a processing head to move the sheath retainer along the longitudinal axis of the post; and
   a drive to rotate the sheath retainer relative to the post, wherein the processing head and the drive are to move the sheath retainer between a first position where the closed end of a first sheath is disposed within a first container and a second position where the closed end of the first sheath is disposed within a second container.

17. The apparatus of claim 16, wherein the first container is a reaction vessel.

18. The apparatus of claim 17, wherein the second container is a wash receptacle.

19. The apparatus of claim 16 further comprising a second sheath, wherein the second sheath is disposed within the second container when the sheath retainer is in the first position.

20. The apparatus of claim 19, wherein the second sheath is disposed within the first container when the sheath retainer is in the second position.

21. The apparatus of claim 6 further comprising a guide plate having a second post aperture to receive the post and a magnetic rod depending from the guide plate.

22. The apparatus of claim 21 further comprising a second lifter coupled to the guide plate to move the guide plate along the longitudinal axis of the post.

23. The apparatus of claim 22, wherein the processing head is to control the first lifter and the second lifter.

* * * * *